(12) United States Patent
Okubo et al.

(10) Patent No.: US 8,978,479 B2
(45) Date of Patent: Mar. 17, 2015

(54) VISCOELASTICITY MEASURING APPARATUS

(75) Inventors: Nobuaki Okubo, Chiba (JP); Kengo Kobayashi, Chiba (JP); Toshihiko Nakamura, Chiba (JP); Hirohito Fujiwara, Chiba (JP)

(73) Assignee: Hitachi High-Tech Science Corporation, Tokyo (JP)

( * ) Notice: Subject to any disclaimer, the term of this patent is extended or adjusted under 35 U.S.C. 154(b) by 114 days.

(21) Appl. No.: 13/402,030

(22) Filed: Feb. 22, 2012

(65) Prior Publication Data

US 2012/0216624 A1 Aug. 30, 2012

(30) Foreign Application Priority Data

Feb. 28, 2011 (JP) ................................. 2011-042847

(51) Int. Cl.
*G01N 3/04* (2006.01)
*G01N 3/32* (2006.01)
(52) U.S. Cl.
CPC .. *G01N 3/04* (2013.01); *G01N 3/32* (2013.01); *G01N 2203/0055* (2013.01); *G01N 2203/0094* (2013.01)
USPC .......................................................... 73/788
(58) Field of Classification Search
CPC ... G01N 3/04; G01N 3/32; G01N 2203/0055; G01N 2203/0094
See application file for complete search history.

(56) References Cited

U.S. PATENT DOCUMENTS 6,386,045 B1 5/2002 Nakamura et al.
2005/0126267 A1* 6/2005 Okubo et al. ................ 73/54.02

FOREIGN PATENT DOCUMENTS

| JP | 62-190437 A | 8/1987 |
| JP | 02-045731 A | 2/1990 |
| JP | 02045731 A | 2/1990 |
| JP | 07-270293 A | 10/1995 |
| JP | 2001-099778 A | 4/2001 |

* cited by examiner

*Primary Examiner* — Lisa Caputo
*Assistant Examiner* — Brandi N Hopkins
(74) *Attorney, Agent, or Firm* — Brinks Gilson & Lione (57) ABSTRACT

Provided is a viscoelasticity measuring apparatus in which an undesirable sample shape change such as a buckle caused as a result of thermal expansion of a sample is eliminated so as to prevent a deformation in a displacement detector direction due to the thermal expansion and a bending of the sample between a sample grasping member and a chuck, to thereby improve accuracy of measurement. In the viscoelasticity measuring apparatus, a thin part is provided in a part of an elastic arm for holding the sample so as to be easily deformed by a thermal expansion force of the sample. Thus, an undesirable shape change such as the buckle generated when the sample is expanded thermally is effectively eliminated, and necessary stiffness is maintained with respect to a load of the sample and hence accuracy of measurement is improved.

4 Claims, 8 Drawing Sheets

FIG. 3C (3a-3a' CROSS SECTION)

FIG. 3D (3b-3b' CROSS SECTION)

(4a-4a' CROSS SECTION)

VISCOELASTICITY MEASURING APPARATUS

RELATED APPLICATIONS

This application claims priority under 35 U.S.C. §119 to Japanese Patent Application No. 2011-042847 filed on Feb. 28, 2011, the entire content of which is hereby incorporated by reference.

BACKGROUND OF THE INVENTION

1. Field of the Invention

The present invention relates to a dynamic viscoelasticity measuring apparatus, which is aimed to improve so-called accuracy of data to be a true value.

2. Description of the Related Art

A dynamic viscoelasticity measuring apparatus (hereinafter, referred to as a DMA) is an apparatus in which distortion or stress changing (oscillating) with time is applied to a sample and the distortion or stress generated in the sample is measured, to thereby analyze mechanical properties of the sample. In many of the apparatus, the sample to be measured is fixed to a holder member. When temperature dependence of the sample is measured and thermal expansion of the sample occurs, because the fixing force of the holder member is larger than the thermal expansion force, there may occur a problem in that the sample is curved. To address the problem, there is known a viscoelasticity apparatus including two sample holder members that do not move in the direction of applying stress or distortion and hold both ends of the sample in such a manner that the sample can be expanded or contracted in the direction connecting both ends by elastic deformation of the sample holder members (see Japanese Patent Application Laid-open No. Hei 02-045731).

In the technology described in Japanese Patent Application Laid-open No. Hei 02-0457321, instead of fixing both ends of the sample in all directions, the ends of the sample are respectively held by individual two sample holder members, which can move in the direction connecting both ends of the sample. Thus, even if the sample has temperature dependence, an accurate calculation result can be obtained without restricting deformation in the direction due to temperature change and without changing the assumption of a sample shape (to be a rectangular solid or a cylindrical column) for calculating a complex elastic modulus. In a specific elasticity modulus measurement, a sine wave generated from a sine wave generator is transmitted to a force generator via an amplifier, and hence a stress in the direction substantially perpendicular to a sample surface of the sample is generated via a detection rod. The stress is detected by a detector fixed to a part of the detection rod, together with distortion generated in the sample. From correlation between the stress and the distortion, the complex elastic modulus is calculated. In calculation of the complex elastic modulus, a precondition and an important factor for calculation accuracy reside in that a sample shape is a rectangular solid or a cylindrical column. Here, in the measurement, heating adjustment is performed by a heating source equipped for adjustment of temperature condition. This heat is transferred to the sample via two sample holder members, a part of an elastic arm, a sample grasping chuck, and a part of the detection rod. As a result, the sample is expanded thermally. Therefore, in order to calculate the complex elastic modulus accurately as described above, it is necessary that the thermal expansion of the sample should occur only in the direction connecting both ends of the sample, and it is necessary to suppress a deformation in the direction (measuring direction) perpendicular to the above-mentioned direction so that the sample can maintain the rectangular solid shape or the cylindrical column shape.

The task described in the above-mentioned conventional technology is to divide the sample holder member into two members at both ends of the sample, and hence to absorb the thermal expansion force of the sample in the direction connecting both ends of the sample. Thus, it is aimed to suppress the deformation in the direction perpendicular to the above-mentioned direction, with the result that the accuracy of data is improved.

Figure 5A:
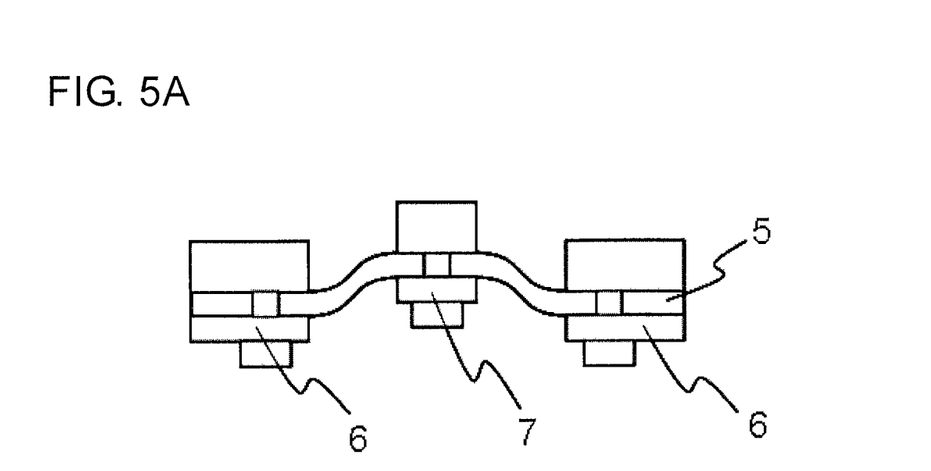
FIGS. 5A and 5B are schematic diagrams of variation examples of a sample, which negatively affect accuracy.
Figure 5B:
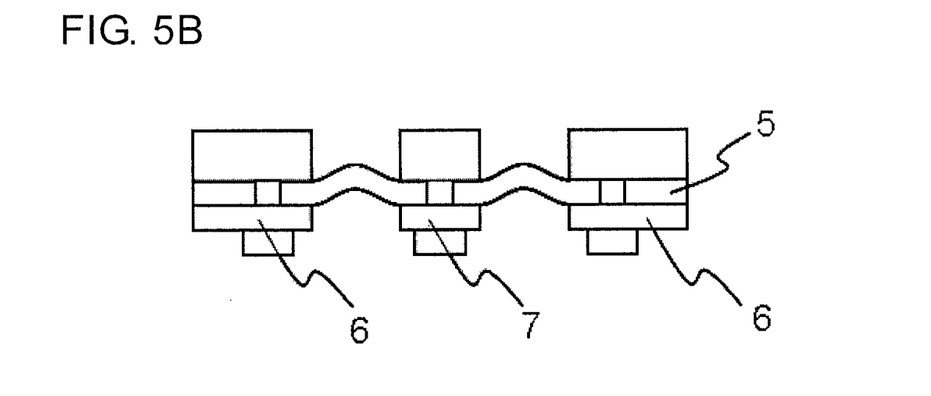
Figure 6:
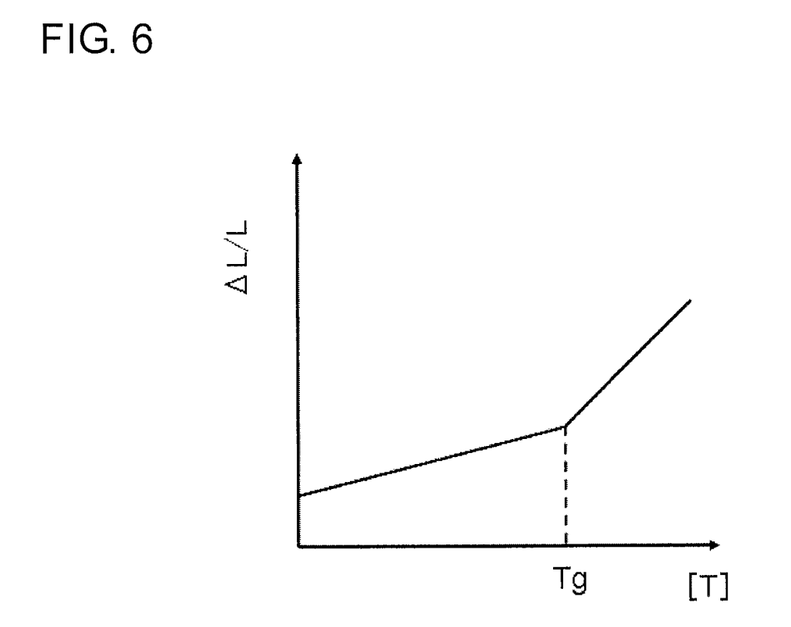
FIG. 6 is a schematic diagram of thermal expansion of a sample before and after a glass transition temperature Tg.

However, if the stiffness of the sample made of polymer material or the like due to expansion is smaller than the stiffness of the elastic arms in the direction connecting both ends of the sample, the distance between the sample holder members does not increase to such an extent corresponding to the expansion of the sample, and hence data accuracy is not improved. In particular, in the region exceeding a glass transition temperature Tg as illustrated in FIG. 6, as the thermal expansion of the sample increases in a discontinuous manner, the sample becomes softened, and the stiffness of the sample decreases. Therefore, the stiffness of the elastic arms becomes relatively large, and hence the elastic arms are not extended in the sample expansion direction for absorbing the thermal expansion of the sample. As a result, there is no absorption of the thermal expansion in the direction connecting both ends of the sample, and the sample cannot maintain its rectangular solid shape or cylindrical column shape any more and thus an undesirable deformation occurs. For example, the sample may be buckled as illustrated in FIG. 5A, or the sample may be bent between the sample holder member and the chuck as illustrated in FIG. 5B. Consequently, it becomes difficult to measure the elasticity modulus as intended, and the data accuracy is deteriorated.

SUMMARY OF THE INVENTION

Therefore, it is an object of the present invention to solve the above-mentioned problem by forming a thin part having a predetermined shape in a part of the elastic arms so that the stiffness decreases only in the direction connecting both ends of the sample and the elastic arms can be easily deformed elastically in the direction, without decreasing the stiffness in the measuring direction of the sample. In this way, an undesirable deformation hardly occurs in the sample. Therefore, the accuracy of the measurement is improved, and the precondition in the calculation step thereafter (that the sample has a rectangular solid shape or a cylindrical column shape) is not broken. Thus, the accuracy of the result is improved.

A viscoelasticity measuring apparatus according to the present invention includes: a chuck that grasps a sample at substantially a central part; a bar-type detection rod that supports the chuck at one end thereof, and is disposed in a thickness direction of the sample; a work effector such as a force generator or a distortion generator disposed at another end of the bar-type detection rod, for applying a load of one of force and distortion to the sample in the thickness direction via the bar-type detection rod and the chuck; a heating source for heating the sample; a sine wave generator that generates a sine wave for causing the force generator to generate work (one of force and distortion) in the form of a sine wave; an amplifier for adjusting an amplitude of the sine wave; a workload detector that is partially fixed to the bar-type detection rod and detects workload of the work; an amplitude comparing detector that compares a signal from the workload detector to a signal from the amplifier so as to output an amplitude ratio; a phase difference detector that compares the signal from the workload detector to the signal from the amplifier so as to output a phase difference; a casing for housing the workload detector and the work effector; a detection rod support member that restricts a movable direction of the bar-type detection rod to a linear direction in the casing and elastically supports the bar-type detection rod; and a sample holder member including a sample holder having a plurality of elastic arms, the plurality of elastic arms having one end fixed to a part of the casing and another end split into at least two portions, the sample holder holding both ends of the sample in the thickness direction, in which the plurality of split elastic arms have thin parts formed in parts thereof so as to suppress deformation of the sample in the direction perpendicular to the direction connecting both ends of the sample. With this structure, even when the sample fixed at both ends by the holder member is expanded by the thermal expansion or the like, the deformation in the viscoelasticity measuring direction is prevented. Therefore, a precondition of a sample shape for calculation of a complex elastic modulus (to be a rectangular solid shape or a cylindrical column shape) is not broken, and it is possible to obtain a result closer to a true value in the measurement. Thus, the complex elastic modulus can be calculated with high accuracy.

In addition, in the present invention, the elastic arm is split into two or four so that reaction force per elastic arm is reduced, while a necessary function is secured by bundling of a plurality of arms. With this structure, the elastic arm can be easily deformed with respect to a deformation of the sample, and hence an influence to the measurement can be reduced.

In addition, in the viscoelasticity measuring apparatus according to the present invention, an elasticity modulus as the stiffness of the elastic arm is set in consideration of a decrease in the elasticity modulus of the sample in a temperature range over a glass transition temperature or a softening temperature. With this structure, when an expanding force of the sample rapidly decreases, as the temperature of the sample exceeds the glass transition temperature or the softening temperature, the deformation of the elastic arm does not become a resistance, and hence the accuracy of the measurement can be maintained.

In addition, in the viscoelasticity measuring apparatus according to the present invention, the size of the above-mentioned thin part provided in a part of the elastic arm can be changed according to the size of the sample and the thermal expansion/contraction characteristics.

According to the viscoelasticity measuring apparatus according to the present invention, a predetermined thin part corresponding to the expanding force of the sample is provided in a part of the elastic arm, and hence the elastic arm can easily be warped through the expansion of the sample in the direction connecting both ends, and thus the independent holder members can move more effectively. Consequently, even when heating is performed, the sample shape such as a rectangular solid shape or a cylindrical column can be maintained, and hence an influence in the measuring direction perpendicular to the direction connecting both ends of the sample, which is mostly important at various temperatures, can be reduced. Therefore, the precondition of the sample shape for calculating the complex elastic modulus is not broken, and a measuring error is not generated. Thus, high accuracy calculation can be performed. In addition, because the elastic deformations of the sample holder members and the elastic arms are utilized, the structure becomes simple, and the periphery of the sample can be designed in compact, and hence equal effects can be obtained both in thermal expansion when heating is performed and in thermal contraction when cooling is performed.

In addition, when the temperature of the sample exceeds the glass transition temperature, the expansion rate increases discontinuously as illustrated in FIG. 6. On the other hand, because the sample is softened, it is necessary for the elastic arm to be warped more easily in the expansion direction of the sample. Therefore, the present invention works more effectively in particular when the measuring viscoelasticity of the sample whose temperature exceeds the glass transition temperature.

DETAILED DESCRIPTION OF THE PREFERRED EMBODIMENT

An embodiment of a stress control type viscoelasticity measuring apparatus according to the present invention is described below with reference to the attached drawings.

Figure 1:
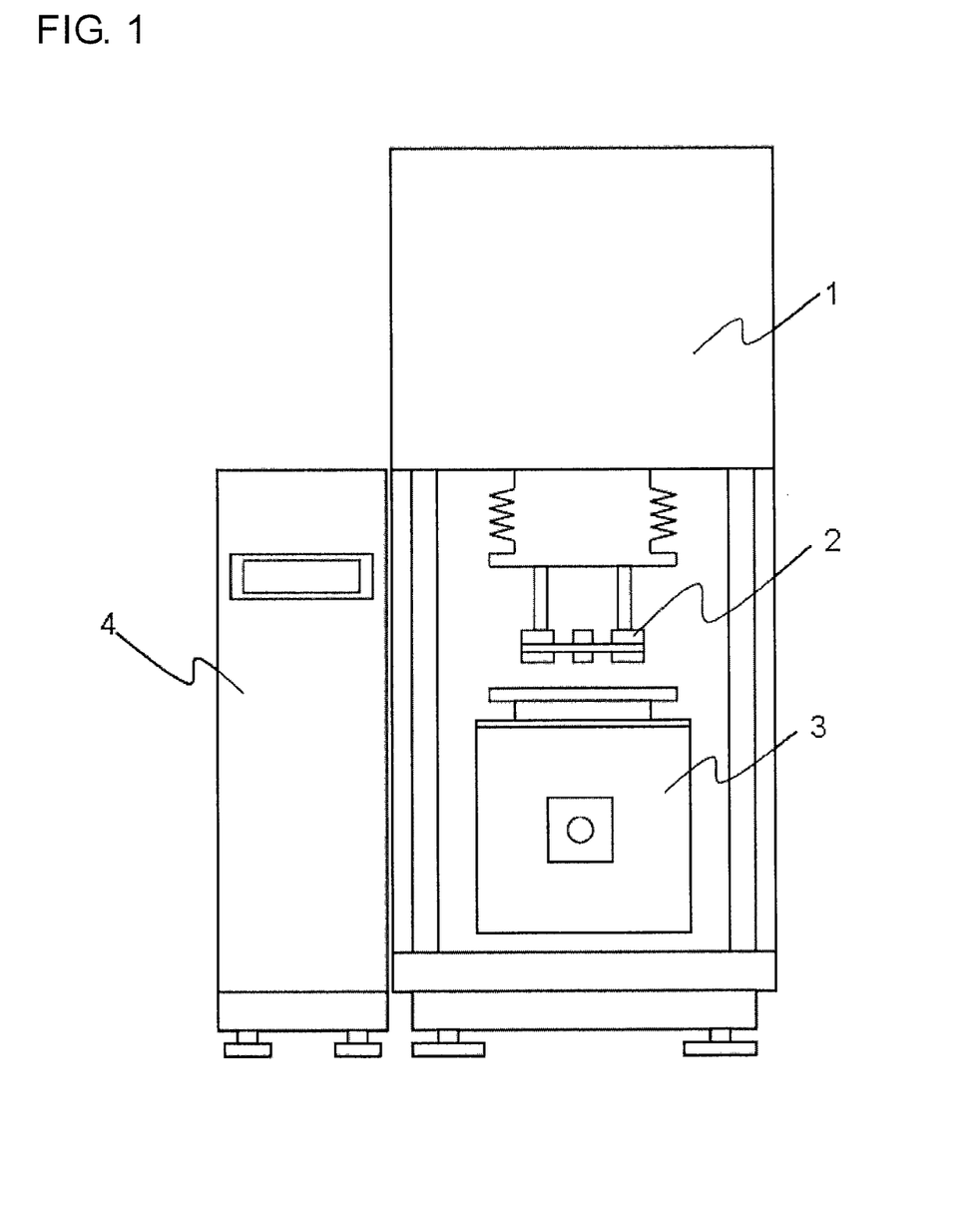
FIG. 1 is a general schematic diagram of a viscoelasticity measuring apparatus according to the present invention.

FIG. 1 is a general schematic diagram of the viscoelasticity measuring apparatus, which includes a work effector and workload detector 1, a sample portion 2 for setting a sample to be measured, a heating furnace portion 3 for heating, and an electrical component portion 4 that performs control and calculation. The heating furnace 3 can be moved up and down. When performing measurement with heating, the heating furnace 3 is moved upward to cover the sample portion 2.

Figure 2:
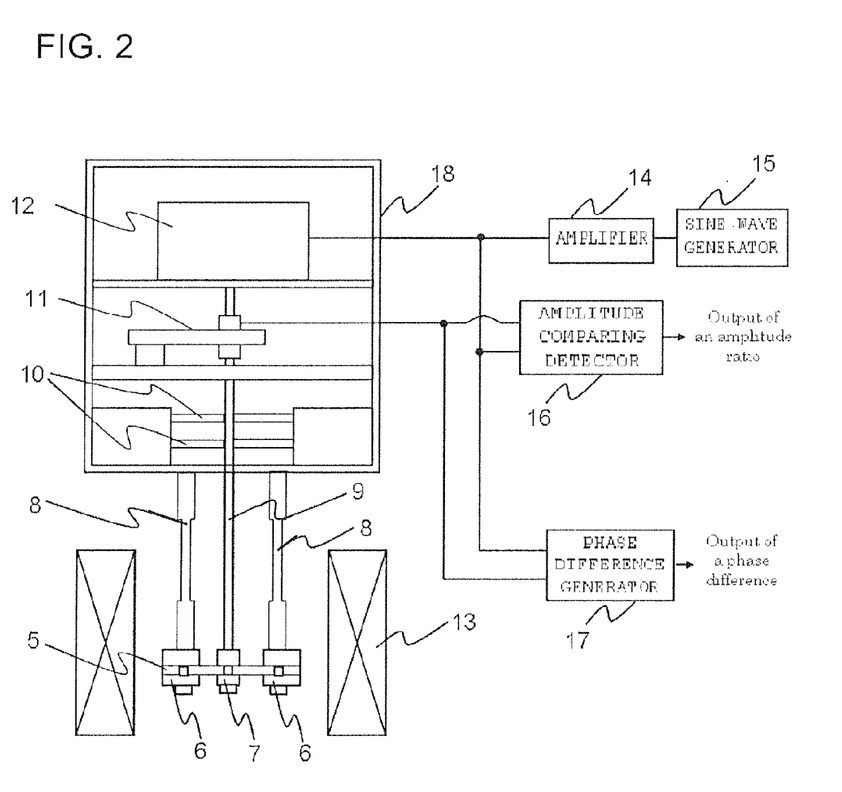
FIG. 2 is a detailed diagram of a main part of a stress control type viscoelasticity measuring apparatus according to the present invention.

FIG. 2 illustrates more details of FIG. 1. In FIG. 2, both ends of a sample 5 are held by sample holder members 6.

The sample holder members 6 are elastically supported by elastic arms 8, respectively, each of which is fixed to a casing 18 at the end.

A chuck 7 grasps the central part of the sample. The chuck 7 is fixed to a detection rod 9, and the detection rod 9 is elastically supported by a detection rod support member 10. In addition, a movable direction of the detection rod 9 is restricted to be linear (one dimension). Further, a displacement detector 11 corresponding to the workload detector is attached to a part of the detection rod 9, which detects a relative position to the casing 18. In addition, a force generator 12 corresponding to the work effector is fixed to one end of the detection rod. On the other hand, around the sample 5, there is disposed a heating source 13 for a purpose of setting a temperature environment of the sample 5.

A sine wave generator 15 illustrated in FIG. 2 generates a sine wave output. The amplitude of the sine wave output is controlled by an amplifier 14, and then the sine wave output is applied to the force generator 12. The output of the amplifier 14 is sent to an amplitude comparing detector 16 and a phase difference detector 17. In addition, an output of the displacement detector 11 is sent to the amplitude comparing detector 16 and the phase difference detector 17. The amplitude comparing detector 16 outputs an amplitude ratio signal, and the phase difference detector 17 outputs a phase difference signal. These two signals (amplitude ratio signal and phase difference signal) have quantities indicating viscoelasticity characteristics as known well. The former indicates the amplitude of complex elastic modulus, and the latter indicates a loss tangent. An action around the sample 5 when the apparatus performs heating according to this embodiment is described. First, the heat from the heating source 13 heats the sample 5, the sample holder members 6, the chuck 7, a part of the elastic arm 8, and a part of the detection rod 9. When the sample is thermally expanded by the heating, the sample holder members 6 are pushed towards both ends, and simultaneously the elastic arms are elastically deformed in the sample expansion direction to be displaced by the thermal expansion amount and hold the sample 5. Therefore, the sample 5 is not deformed in the direction parallel to the detection rod and is deformed only in the sample expansion direction of the sample 5 and thus the sample 5 maintains the rectangular solid shape or the cylindrical column shape.

Here, FIGS. 5A and 5B illustrate examples of deformation of the sample 5 in a case where stiffness of the elastic arm 8 is excessively high. FIG. 5A illustrates an example in which the sample 5 is buckled by the force generated by expansion of the sample 5, and the chuck 7 is pressed upward to be higher than the sample holder member 6. FIG. 5B illustrates an example in which a relative position between the chuck 7 and the sample holder member 6 is not changed, but the sample 5 is bent between the chuck 7 and the sample holder member 6 by the force generated by expansion of the sample 5. If one of the deformations of the sample illustrated in FIGS. 5A and 5B occurs, it becomes difficult to perform elasticity measurement correctly.

Figure 4A:
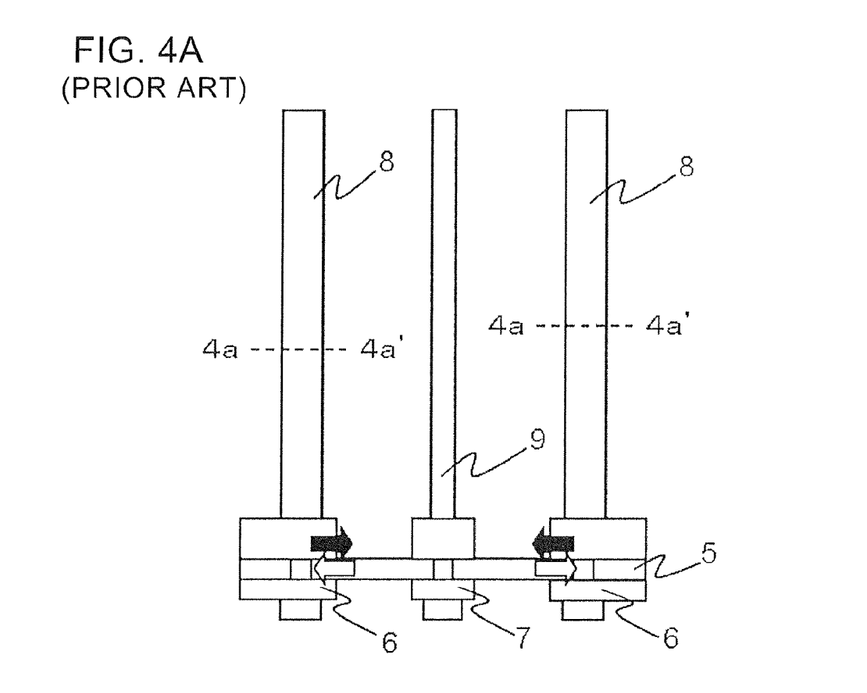
FIG. 4A is a front view of a conventional elastic arm.
Figure 4B:
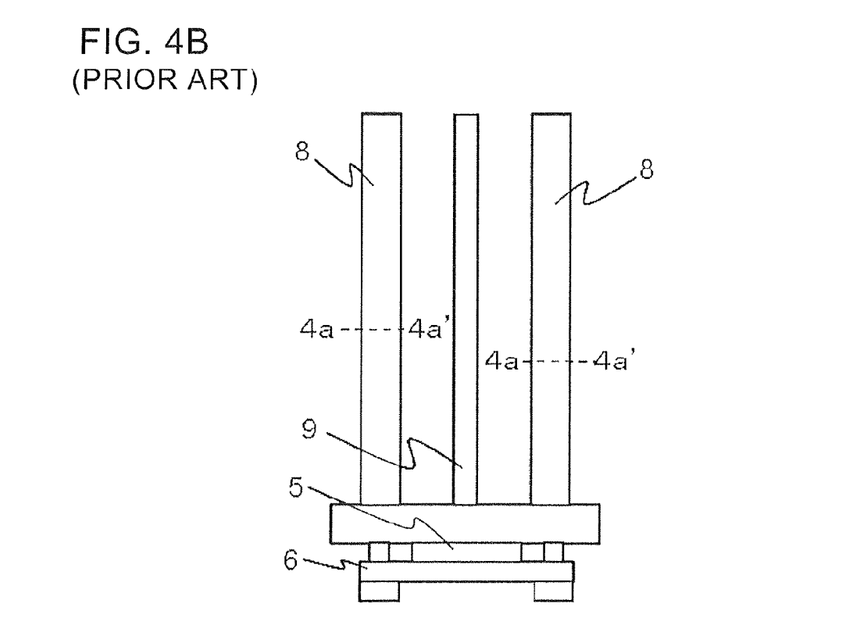
FIG. 4B is a side view of the conventional elastic arm.
Figure 4C:
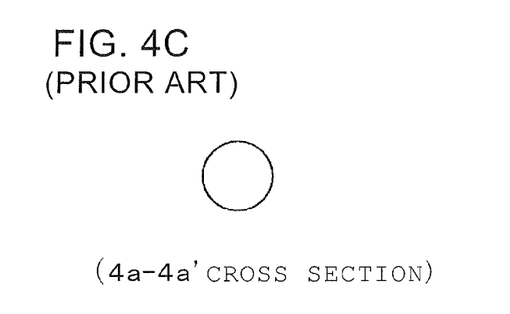
FIG. 4C illustrates a cross-sectional shape taken along line $4a$-$4a'$.

In this way, the above-mentioned deformation of the sample occurs when the stiffness of the elastic arm is high in the sample expansion direction as illustrated in FIGS. 4A to 4C. FIG. 4A is a front view of the elastic arms 8 of the conventional viscoelasticity measuring apparatus, FIG. 4B is a side view of the elastic arms 8 of the conventional viscoelasticity measuring apparatus, and FIG. 4C illustrates a cross-sectional shape taken along line 4a-4a'. The arrow direction in the diagram indicates the direction in which the force is applied, and a size of the arrow indicates the magnitude of the force. In addition, the white arrow indicates a force generated by expansion of the sample 5, and the black arrow indicates a force necessary for the elastic arm 8 to warp. As understood from these diagrams, the elastic arm 8 has the same thickness in all directions with high stiffness and is hardly deformed in the expansion direction of the sample. As a result, the force due to the expansion of the sample 5 is balanced with the force necessary for the elastic arm 8 to warp. Therefore, the deformations of the sample as illustrated in FIGS. 5A and 5B are induced.

FIG. 6 is a schematic diagram of thermal expansion of the sample in a temperature region including a general glass transition temperature. A length to be a reference of the sample is denoted by L, a length changed from a reference value L of the sample is denoted by ΔL, temperature is denoted by T, and the glass transition temperature is denoted by Tg. Therefore, the vertical axis represents storage elastic modulus. In this way, when the sample exceeds the glass transition temperature, the expansion rate increases discontinuously, and the storage elastic modulus rapidly decreases. Alternatively, in the sample having the fixed softening temperature, it is necessary to consider a change of elasticity modulus of the sample before and after the softening temperature in the same manner. Therefore, a force of expansion of the sample largely decreases in a temperature range exceeding the glass transition temperature or the softening temperature. Thus, it is also considered to sufficiently decrease the elasticity modulus as stiffness of the elastic arm so as to set in multiple values.

EXAMPLE

Figure 3A:
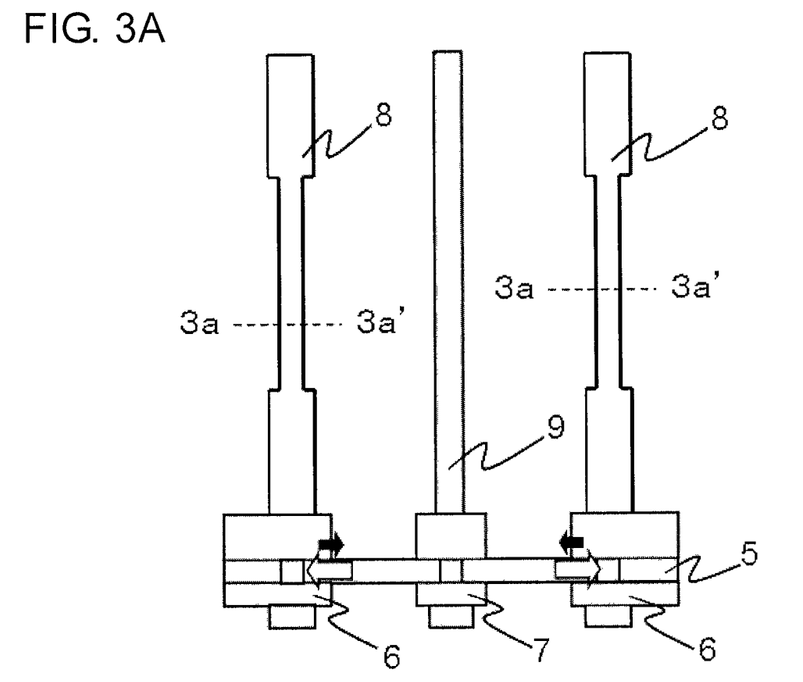
FIG. 3A is a front view of elastic arms according to the present invention.
Figure 3B:
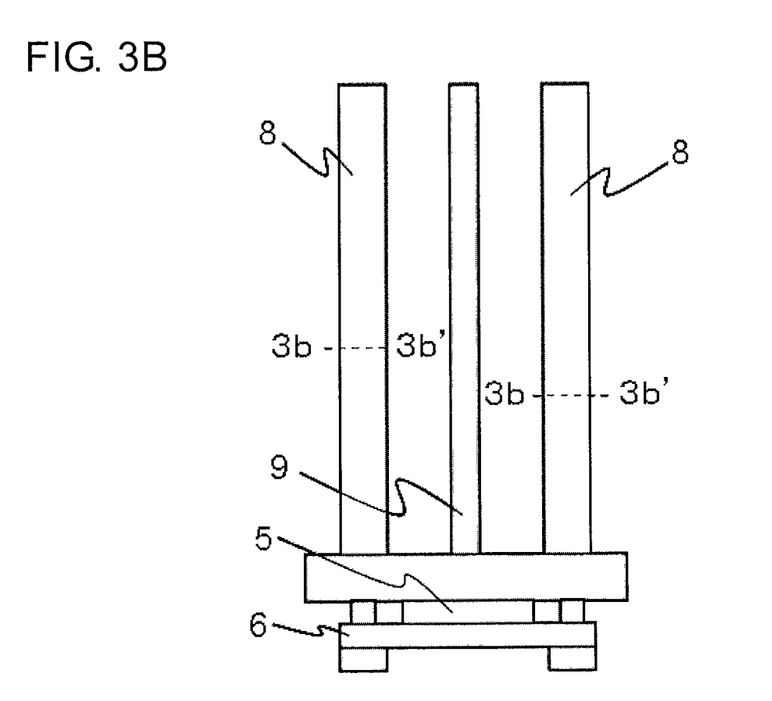
FIG. 3B is a side view of the elastic arms according to the present invention.
Figure 3C:
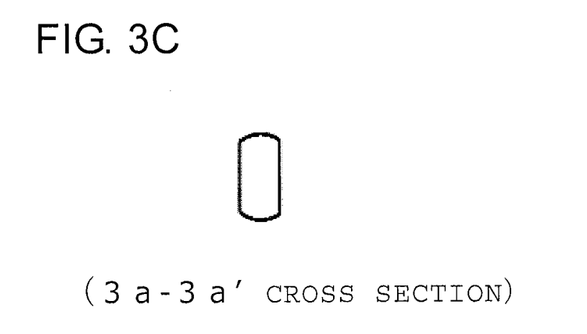
FIG. 3C illustrates a cross-sectional shape taken along line $3a$-$3a'$.
Figure 3D:
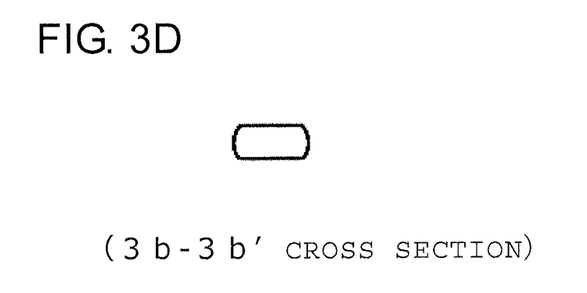
FIG. 3D illustrates a cross-sectional shape taken along line $3b$-$3b'$.

FIGS. 3A to 3D illustrate the elastic arms 8 having a defined shape so that stiffness in the sample expansion direction decreases, and the peripheral members. FIG. 3A is a front view of the elastic arms 8 of the viscoelasticity measuring apparatus according to the present invention, FIG. 3B is a side view of the elastic arms 8 of the viscoelasticity measuring apparatus according to the present invention, FIG. 3C illustrates a cross-sectional shape taken along line 3a-3a', and FIG. 3D illustrates a cross-sectional shape taken along line 3b-3b'. The arrow direction in the diagram indicates a direction in which a force is applied, and a size of the arrow indicates the magnitude of the force. In addition, the white arrow indicates the force generated by expansion of the sample 5, and the black arrow indicates the force necessary for the elastic arm 8 to warp. As understood from FIG. 3A, the elastic arm 8 is formed to be thin in the sample expansion direction.

Thus, stiffness of the elastic arm 8 in the sample expansion direction decreases, and hence the elastic arm 8 is easily warped in the sample expansion direction. In addition, the force necessary for the elastic arm 8 to warp is smaller than the force due to expansion of the sample 5.

In this example, both sides of the elastic arm 8 having a diameter of 8 mm are cut down by 2 mm each, and hence the elastic arm 8 has a width of 4 mm only in the expansion direction of the sample as illustrated in FIGS. 3C and 3D.

In this case, a change of stiffness as a result of decreasing the thickness is determined as a spring constant by structural analysis calculation. The spring constant of the elastic arm 8 having a diameter of 8 mm is $5.91 \times 10^5$ N/m, and the spring constant of the elastic arm 8 in which both the sides of the elastic arm 8 having a diameter of 8 mm are cut down by 2 mm each is $1.49 \times 10^5$ N/m. Therefore, the spring constant decreases by approximately 75%. On the other hand, it is supposed that the sample 5 is made of poly methyl methacrylate (PMMA). Then, the elasticity modulus at the glass transition temperature and the vicinity is approximately $6 \times 10^8$ Pa. The spring constant of the sample 5 is determined to be $1.8 \times 10^6$ N/m from the elasticity modulus of the sample 5 and a form factor $\alpha = 3 \times 10^{-3}$ m of the sample 5. The spring constant of the elastic arm 8 of 8 mm is approximately ⅓ of the spring constant of the sample 5, and the spring constant of the thinned elastic arm 8 of 4 mm is approximately ¹⁄₁₀ of that of the sample 5 and thus the stiffness of the elastic arm decreases effectively.

In addition, when the shape of the sample 5 supposed to be made of PMMA is changed so that the form factor $\alpha = 8.0 \times 10^4$ m, the spring constant of the sample 5 decreases to $4.8 \times 10^5$ N/m, which is approximately ¼. In this case, the spring constant of the elastic arm 8 of 8 mm is larger than the spring constant of the sample 5, and the spring constant of the thinned elastic arm 8 of 4 mm is smaller than the spring constant of the sample 5. In other words, it is understood that, with the elastic arm 8 cut down in thickness, the viscoelasticity measuring apparatus can support various sample shapes even for the same sample.

Note that, the width of the elastic arm 8 is not limited to the above-mentioned cut-down width, and it is possible to select an elastic arm width having different stiffness values in accordance with samples to be measured. As a result of decreasing the stiffness of the elastic arm, the elastic arm 8 is warped in the sample expansion direction when the sample 5 is expanded. Therefore, stress in the sample is reduced and hence deformation of the sample illustrated in FIG. 5A is hardly generated as described later. As a result, a measurement error is reduced, and high accuracy measurement can be performed. In addition, as illustrated in FIG. 3B, the thickness of the elastic arm 8 in the direction that has no relation to expansion of the sample is not changed and hence the stiffness in the direction parallel to the loading direction of the sample 5 does not decrease.

In addition, the shape of the elastic arm 8 is the cylindrical column in this embodiment, but the cross-sectional shape thereof is not limited to a specific shape, and may be an ellipse or other round shape, or a polygon such as a square. It is needless to say that any shape of the elastic arm 8 is included in the technical concept of the present invention as long as the shape of the elastic arm 8 has a structure of forming the thin part of the elastic arm at a part to which a force due to deformation of the sample is applied, so as to obtain the effect of eliminating a substantial influence to the sample in the measuring direction.

What is claimed is:

1. A viscoelasticity measuring apparatus, comprising:
   a chuck that grasps a sample at substantially a central part;
   a bar-type detection rod that supports the chuck at one end thereof and is disposed in a thickness direction of the sample;
   a work effector disposed at another end of the bar-type detection rod, for applying a load of work to the sample in the thickness direction via the bar-type detection rod and the chuck;
   a heating source for heating the sample;
   a sine wave generator that generates a sine wave for causing the work effector to generate work in the form of a sine wave;
   an amplifier for adjusting an amplitude of the sine wave;
   a workload detector that is partially fixed to the bar-type detection rod and detects workload of the work;
   an amplitude comparing detector that compares a signal from the workload detector to a signal from the amplifier so as to output an amplitude ratio;
   a phase difference detector that compares the signal from the workload detector to the signal from the amplifier so as to output a phase difference;
   a casing for housing the workload detector and the work effector;
   a detection rod support member that restricts a movable direction of the bar-type detection rod to a linear direction in the casing and elastically supports the bar-type detection rod; and
   a plurality of sample holder members supported by a plurality of elastic arms, each of the plurality of elastic arms having an upper end portion extending to one end fixed to a part of the casing and a lower end portion extending to another end supporting a sample holder member, the plurality of sample holders holding both ends of the sample in the thickness direction,
   wherein the plurality of elastic arms has a cross-sectional shape in at least a substantially middle portion thereof that is thinner in a direction of thermal expansion of the sample than in a direction perpendicular to the thermal expansion direction of the sample and the substantially middle portion of each of the plurality of elastic arms arm is thinner in the direction of thermal expansion of the sample than the upper end portion thereof and the lower end portion thereof.

2. A viscoelasticity measuring apparatus according to claim 1, wherein the work effector and the workload detector comprise one of:
   (i) a force generator that applies a load of force in the thickness direction of the sample and a displacement detector that detects a position of the bar-type detection rod, respectively; and
   (ii) a distortion generator that applies a load of distortion in the thickness direction of the sample and a stress detector that detects a stress loaded to the sample, respectively.

3. A viscoelasticity measuring apparatus according to claim 1, wherein the plurality of elastic arms each have an elasticity modulus that is lower than an elasticity modulus of the sample in a temperature region of a glass transition temperature or higher.

4. A viscoelasticity measuring apparatus according to claim 1, wherein the plurality of elastic arms each have an elasticity modulus that is lower than an elasticity modulus of the sample in a temperature region of a softening temperature or higher.

\* \* \* \* \*

UNITED STATES PATENT AND TRADEMARK OFFICE
CERTIFICATE OF CORRECTION

PATENT NO.         : 8,978,479 B2
APPLICATION NO.    : 13/402030
DATED              : March 17, 2015
INVENTOR(S)        : Nobuaki Okubo et al.

Page 1 of 1

It is certified that error appears in the above-identified patent and that said Letters Patent is hereby corrected as shown below:

In the Claims

In column 8, claim 1, line 17, after "wherein" insert --each of--.

Signed and Sealed this
Twenty-seventh Day of October, 2015

Michelle K. Lee
*Director of the United States Patent and Trademark Office*